(12) United States Patent
Caldwell

(10) Patent No.: US 7,169,112 B2
(45) Date of Patent: Jan. 30, 2007

(54) NON-CONTACT RESPIRATION MONITOR

(75) Inventor: Donald W. Caldwell, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/936,992

(22) Filed: Sep. 9, 2004

(65) Prior Publication Data

US 2005/0065449 A1 Mar. 24, 2005

Related U.S. Application Data

(60) Provisional application No. 60/501,403, filed on Sep. 10, 2003.

(51) Int. Cl.
*A61B 5/00* (2006.01)
(52) U.S. Cl. ...................... 600/533; 600/538
(58) Field of Classification Search ........ 600/529–538; 128/205.27–205.29, 206.11–206.2
See application file for complete search history.

(56) References Cited

U.S. PATENT DOCUMENTS

| | | | | |
|---|---|---|---|---|
| 4,827,924 A | * | 5/1989 | Japuntich | 128/206.12 |
| 5,063,938 A | * | 11/1991 | Beck et al. | 600/537 |
| 5,383,470 A | * | 1/1995 | Kolbly | 600/538 |
| 5,857,460 A | * | 1/1999 | Popitz | 128/206.21 |
| 6,468,222 B1 | * | 10/2002 | Mault et al. | 600/531 |
| 6,895,962 B2 | * | 5/2005 | Kullik et al. | 128/204.18 |
| 2002/0062830 A1 | * | 5/2002 | Meier et al. | 128/206.12 |
| 2003/0004427 A1 | * | 1/2003 | Swisa | 600/539 |
| 2004/0163648 A1 | * | 8/2004 | Burton | 128/204.21 |
| 2004/0233058 A1 | * | 11/2004 | Dodds | 340/573.1 |

* cited by examiner

*Primary Examiner*—Robert L. Nasser
(74) *Attorney, Agent, or Firm*—Elizabeth Arwine

(57) ABSTRACT

This invention relates to non-contact monitoring devices, and more particularly, non-contact respiration monitoring devices. According to the invention there is provided a monitoring device having a body defining an air monitoring channel between an air inlet and an air outlet. Disposed in monitoring channel is a respiration detection means, such as a flap-valve, which operates with associated logic circuitry to report the presence or absence of respiration via visual and audible displays. The device may be configured to attached, or be integrally connected to, the air input orifice of an air filter canister of a gas mask or the like. Alternatively, the device may be associated with the air output orifices or valves of a gas mask or the like.

23 Claims, 3 Drawing Sheets

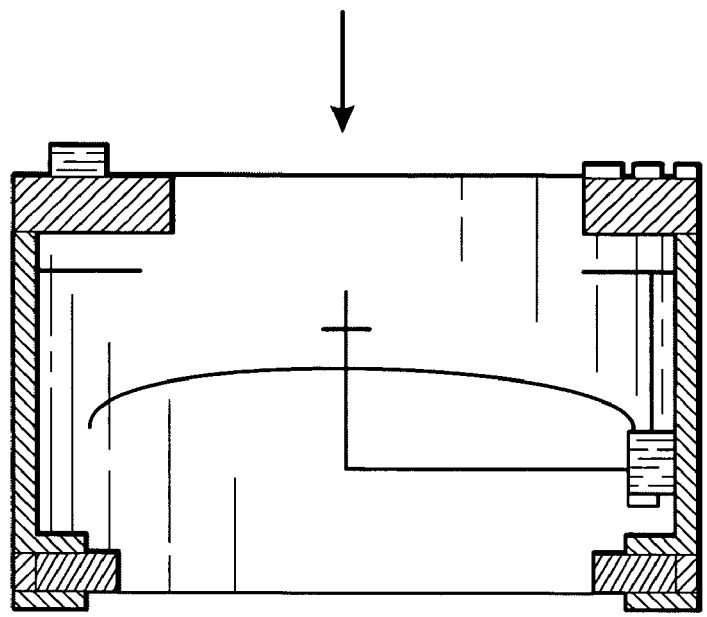
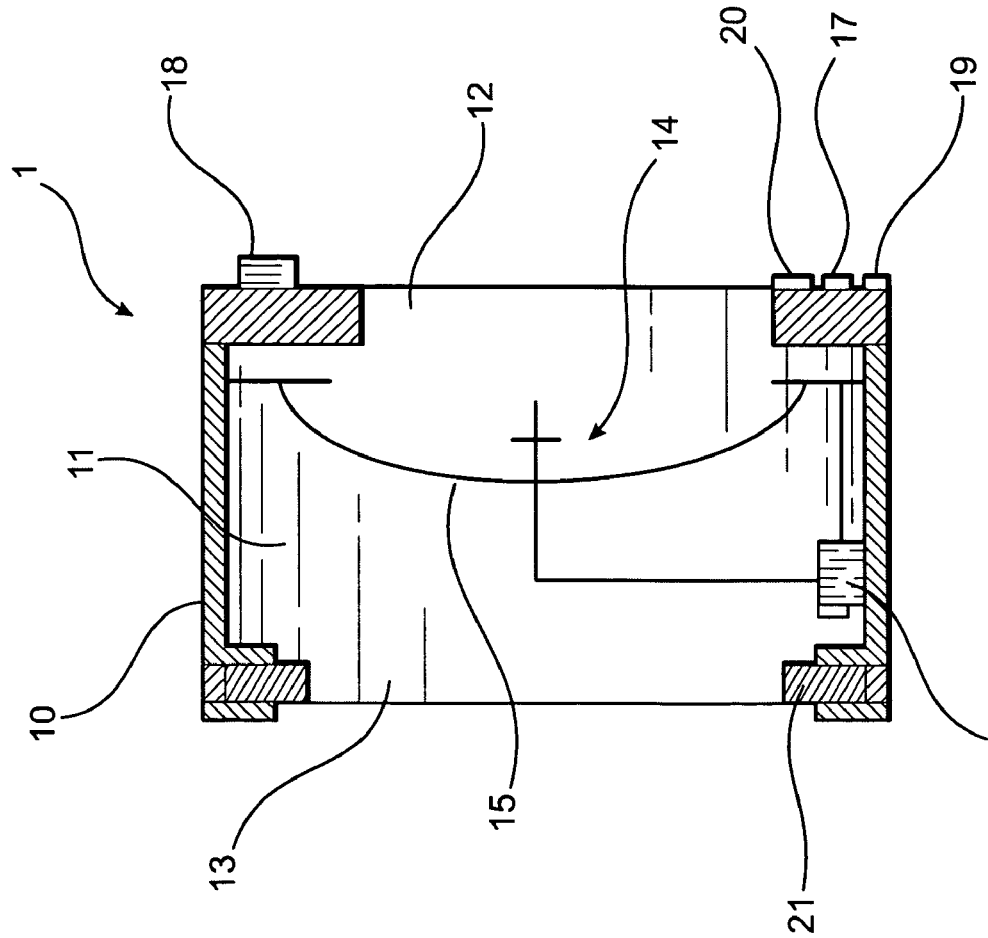

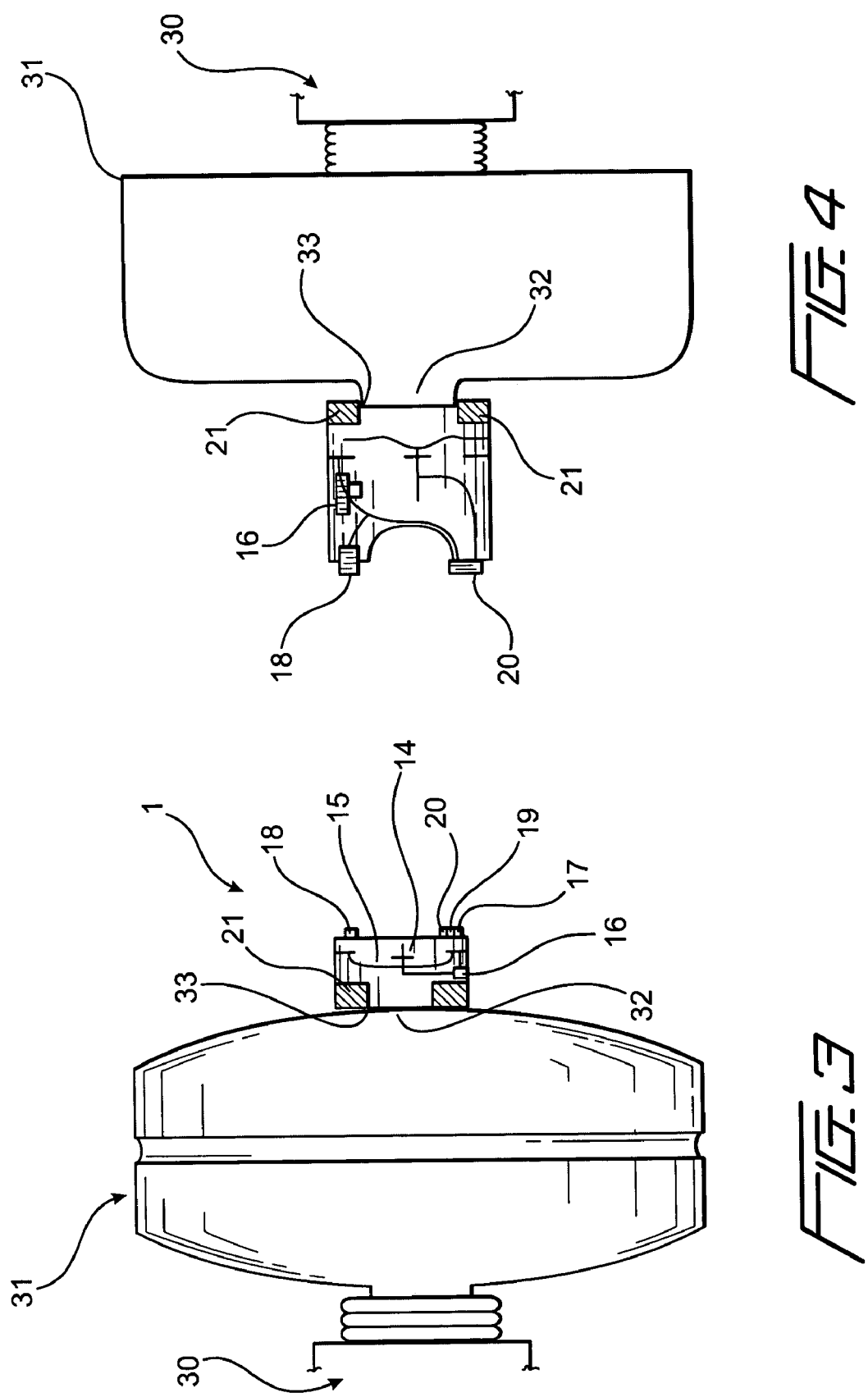

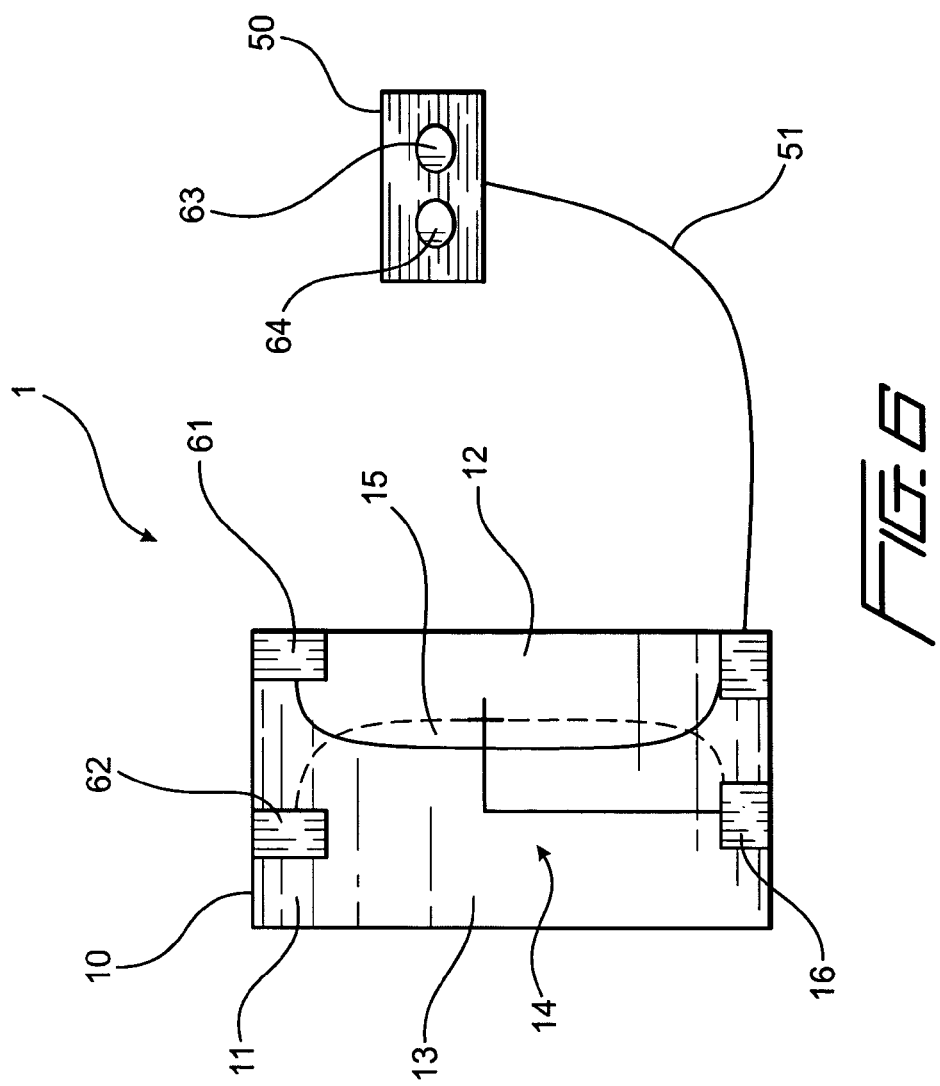
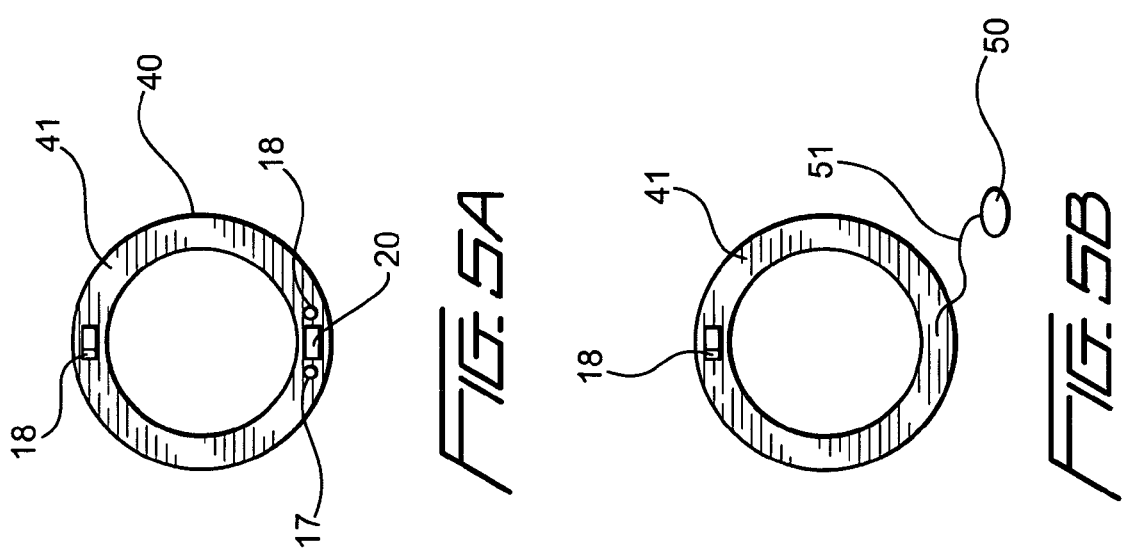

NON-CONTACT RESPIRATION MONITOR

This application claims the benefit of priority under 35 U.S.C. § 119(e) from U.S. Application Ser. No. 60/501,403 filed Sep. 10, 2003.

FIELD OF THE INVENTION

The present invention relates to devices for detecting or monitoring a vital of a patient. More particularly, the present invention relates to a device for detecting or monitoring the respiration of a patient.

BACKGROUND OF THE INVENTION

Determining whether an unconscious patient's heart is beating and whether the patient is breathing are the two most important vital signs in an emergency situation. In many situations, rescuers can check these vitals by touching the individual with their hands or an instrument, such as a stethoscope. However, as will be appreciated, there are situations and environments where contacting the patient's body with hands or instruments is not recommended or feasible. One particular example involves situations where a patient loses consciousness while in protective gear, such as chemical gear, which, obviously, cannot be removed to allow access to the body of the wearer without risk of exposing the patient to the environment the protective gear is protecting the patient from. In these situations, the patient typically has to be removed to a safe environment before the protective gear can be removed and the condition and vitals of the patient examined.

There are devices for continuously detecting and monitoring a patient's vital signs in chemical gear, or otherwise, known in the art. Typically, these devices are monitors operatively associated with the wearer such that the vital to be detected may be sensed and continuously transmitted to a remote receiver in a safe area. For example, a pulse monitor may be attached to the wearer and adapted to broadcast the wearer's pulse rate to a remote receiver for monitoring the wearer's pulse. These prior art devices are used in numerous fields for a wide variety of applications where continuous monitoring of the condition of a subject is important.

A device for detecting (or monitoring) the pulse of a patient is extremely important in emergency situations. Various treatment options depend on the existence and/or strength of the patient's pulse. For example, a person without a detectable pulse requires immediate life-saving measures to be undertaken. Accordingly, it is desirable to provide remote monitors for pulse and/or other vitals in connection with chemical protective gear. However, there are situations where this is unfeasible. For example, take the modern battlefield. Modern warfare and weapons of mass destruction pose severe risk of mass casualty situations involving soldiers (and possibly civilians) wearing protective gear, such as for example, Level IV MOPP gear or gas masks. It is difficult to attempt to remotely monitor continuous broadcasts of the vitals of a battlefield full of soldiers wearing protective gear that sends out signals of the wearer's vital(s). Accordingly, as will be appreciated, in the unfortunate event of a catastrophic incident resulting in mass casualties, there is no way of triaging the condition of an unconscious patient in view of the fact that the protective masks and/or garments cannot be removed to allow detection of pulse or respiration until the patient is moved out of harms way. In such a catastrophe, numerous lives may be lost as medical personnel and rescuers cannot determine which unconscious soldiers have a pulse and which do not, and therefore, which soldiers to extract from the battlefield first.

Similar problems, yet on a smaller scale, are faced by firefighting personnel wearing supplied-air masks. Typically, rather than monitor the vital signs of firefighters, their gear is equipped with certain sensors having audible alarms. The most common sensor utilized by firefighters projects a loud audible alarm (and strobe light) if the wearer has not moved in a given span of time. Such an alarm indicates to other firefighters that the individual may be trapped under debris, may need assistance, or may be unconscious. One drawback with these devices is that it does not allow others to determine the vitals of the wearer, instead only the lack of movement. These devices are simply alarms to allow others to find the individual needing assistance (despite low visibility) and extract them to safety for further treatment. As will be appreciated, these devices are ill-suited for the battlefield for a number of reasons. First, soldiers often lie motionless for extended periods to avoid detection or otherwise. Secondly, and more importantly, in mass casualty situations such as those on a battlefield, alarms indicating the lack of movement are of no use. It is not the movement of the soldier, but rather the soldier's condition, that is critical to evaluate immediately.

The foregoing underscores some of the disastrous consequences associated with conventional prior art devices for detecting or monitoring the vital(s) of a patient. Furthermore, the foregoing highlights the critical, yet unresolved need in the art for a device and method for detecting and/or monitoring the vital(s) of a patient wearing protective gear.

SUMMARY OF THE INVENTION

The present invention overcomes the serious practical problems described above and offers new advantages as well. One object of the invention is to provide a non-contact device for detecting a vital of a patient. According to this object of the invention, one aspect of the invention is to provide a device for detecting the vital of a patient wearing protective gear, such as a gas mask. According to this object, another aspect of the invention is to provide a device for detecting respiration of a patient wearing protective gear, such as a gas mask. According to these aspects of the invention, one advantageous feature of the invention allows the device to monitor a vital of a patient. In one preferred embodiment, the device provides visual confirmation of the presence or absence of respiration in a patient. In another preferred embodiment, the device provides audible confirmation of the presence or absence of respiration of a patient. In yet another preferred embodiment, the device provides quantitative information concerning the respiration of a patient.

Another object of the invention is to provide a non-contact device such as those described above which may be selectively associated with a patient to detect a vital of the patient. According to this object of the invention, one aspect of the invention is to provide a device which may be removably coupled to the mask of a patient to detect the presence or absence of a vital. According to this object, another aspect of the invention is to provide a portable device which a user may couple to a patient's gas mask to detect the presence or absence of respiration and then remove the device.

It is yet another object of the invention to provide a non-contact device such as those described above which is coupled to, associated with, or integrated into, protective gear for indicating the status of a vital. According to this object of the invention, one aspect of the invention is to provide protective gear having a built-in device which indicates the presence or absence of respiration in the wearer. According to this object, another aspect of the invention is to provide protective gear, such as a gas mask, which has a device integrated therewith, for determining the respiration of a wearer when the device is turned on by another person. It is another aspect of the invention to provide a device that turns on in response to a respiration event of a wearer and, preferably, then indicates visually, audibly or otherwise that the wearer is (or perhaps is not) breathing.

These and other objects, aspects and features of the invention may be realized by a non-contact respiration monitor including a body having an air inlet, an air outlet, and a means for detecting air flow between the inlet and the outlet. According to one embodiment of the invention, the means for detecting air flow includes a flap-valve. According to another embodiment, the means for detecting air flow includes a flap-valve switch. Preferably, the flap-valve switch is actuated by air flow caused by respiration. According to a preferred embodiment, the flap-valve switch is a flexible electrically-conducting switch which senses air flow through the body of the device.

According to another embodiment of the invention, the device includes a battery-powered logic circuit associated with the flap-valve switch. Preferably, the battery-powered logic circuit uses miniature batteries. In a preferred embodiment, the device is provided with an on/off switch, and more preferably, the switch is associated with the battery circuit. In an alternative embodiment, the device does not have a manually activated on/off switch but is automatically activated when attached to a mask, filter canister, or the like, of a patient to be monitored. More preferably, the device is turned on in response to movement or actuation of the switch caused by a respiration event.

According to another embodiment of the invention, the device is provided with lamps, bulbs, lights or the like, which illuminate if air flow is sensed. Alternatively, the device may be configured such that lamps are illuminated and then dim if air flow is sensed. In either embodiment, it is preferable that movement of inhalation air operates to not only move the flap to cause the circuit to sense respiration, but also to move the flap to operate lamps. In a preferred embodiment, lamps may include an LED.

According to another embodiment of the invention, the device may be configured to provide a numerical display using an LED or any other visually sensed medium. Preferably, the numerical display depicts the breathing rate. Alternatively, the display may be configured by known means to depict other respiration parameters. In a preferred embodiment, the numerical display or visual display features of the invention are provided on a display unit which is removable from the monitor body to allow placement for optimal visibility by a user, such as a medic.

According to a preferred embodiment of the invention, the device is provided with a plurality of lamps or LEDs which illuminate in response to the position of the flap valve. According to this embodiment, for example, a contact may be provided in the device which is contacted by the flap valve during a respiration event. Engaging contact preferably completes a circuit which results in a green lamp being illuminated. Likewise, a contact may be provided which remains in engagement with flap valve unless respiration moves the flap out of communication with the contact. Preferably, if flap valve remains closed a circuit is completed which results in a red lamp being illuminated. Accordingly, determining the condition of the patient becomes readily apparent to a user of the device. As will be appreciated, a number of devices may be used in a mass casualty situation. For example, a medic may connect 10 devices to 10 different casualties and then quickly scan the area for to determine those individuals who are breathing and those who are not breathing.

According to another embodiment of the invention, the device may be configured to provide an audible alarm. Preferably, the alarm sounds if respiration is not sensed by the device. Alternatively, the alarm may be configured to sound if respiration is not sensed for a given period of time or if respiration is sensed within a given period of time. In a preferred embodiment, the device includes both an audible and visual indication of the presence or absence of respiration. More preferably, the device includes an audible alarm indicating the presence or absence of respiration, a visual indication of the presence or absence of respiration, and a visual display of respiration rate.

According to yet another aspect of the invention, the device is configured to send a signal to a remote location that the wearer is (or is not) breathing. According to this aspect of the invention, the device allows for remote monitoring of aspects such as the type and rate of respiration.

According to another aspect of the invention, the body of the monitor is adapted for fluid tight engagement with the filter canister of a gas mask. According to one aspect of the invention, the body is configured to mate with, or surround, the input air orifice of a filter canister. In accordance with a presently preferred embodiment, the device includes a seal or grommet of rubber or like material for facilitating fluid tight connection to the input air orifice. According to another aspect of the invention, the body is configured to surround all or a portion of the body of an air filter canister. In a preferred embodiment, the body of the device includes a material and configuration which provides for fluid-tight coupling to different sizes and shapes of canisters or, alternatively, orifices. In alternative embodiments, the monitor is operatively associated with air outlet orifices or valves of gas masks and the like.

According to another aspect of the invention, the monitor of the present invention is adapted for use on patients without any masks or with only paper masks. In accordance with this aspect of the invention, the monitor may simply surround the mouth and/or nares of a patient, whether or not the patient is wearing a paper mask, and operate along the principles outlined above. One of ordinary skill in the art will appreciate circumstances under which non-contact respiration detection or monitoring of individuals or a mass of individuals may benefit from the present invention.

Another object of the invention is to provide methods of using the monitoring devices described above, and to provide methods of determining or monitoring the respiration of a patient.

Given the following enabling description of the drawings, the apparatus should become evident to a person of ordinary skill in the art.

BRIEF DESCRIPTION OF THE DRAWINGS

The present invention is described with reference to the accompanying drawings. In the drawings, like reference numbers indicate identical or functionally similar elements.

FIG. 1 is a cross-sectional view of a non-contact respiration monitor according to the invention with the flap-valve in the closed position.

FIG. 2 is a cross-sectional view of a non-contact respiration monitor according to the invention with the flap-valve in the open position.

FIG. 3 depicts a non-contact respiration monitor according to the invention coupled to the inlet orifice of an air filter canister of a gas mask.

FIG. 4 depicts the electrical connections of a non-contact respiration monitor coupled to the inlet orifice of an air filter canister of a gas mask.

FIG. 5A is a front view of a removable outer portion of a non-contact respiration monitor according to the invention.

FIG. 5B is a front view of a non-contact respiration monitor according to the invention having a removable display.

FIG. 6 is a cross sectional view of a preferred embodiment of a non-contact respiration monitor according to the invention.

DETAILED DESCRIPTION OF THE DRAWINGS

The present invention is based, in part, on the recognition that the detection and/or monitoring of respiration in a patient is a suitable surrogate for the detection and monitoring of the patient's pulse for purposes of triage in certain situations. While the present invention will be described in connection with a non-contact respiration monitor for use with an air filter canister, it will be readily apparent to one of ordinary skill in the art that the present invention can be applied to a multiplicity of fields and uses. Furthermore, while the present invention will be described in connection with the air input orifice or input of an air filter canister, one of ordinary skill in the art will recognize the interchangeability and ease to which the device can be used with an air output orifice or valve. Finally, while the present invention will be described in connection with a flap-valve switch for detecting respiration, one of ordinary skill in the art will recognize that any suitable means for sensing airflow through a channel are within the scope of the invention.

FIGS. 1–4 depict a presently preferred embodiment of the invention. As shown, non-contact respiration monitor 1 includes body 10 defining air monitoring passageway 11 between air flow inlet 12 and air flow outlet 13. Disposed in air monitoring passageway 11 and between the air flow inlet 12 and outlet 13 is flexible electrically conducting flap-valve switch 14. Flap-valve switch 14 is designed such that air passing from inlet 12 to outlet 13 moves flap 15 from the closed position (shown in FIG. 1) into the open position (shown in FIG. 2). Movement of flap 15 into the open position actuates switch which is detected by battery-powered logic circuit 16 and reported as a respiration event. Logic circuit 16 actuated by flap 15 and logic circuit reports the respiration event by illuminating lamp(s) 17 disposed on an outer surface of air flow inlet 12. Preferably, logic circuit 16 only reports events when the device is activated by a user turning on/off switch 18 to the "on" position (thereby powering the reporting features of the device). In a preferred embodiment, battery-powered logic circuit 16 is also configured to provide an audible alarm from speaker 19 if the device is powered and no movement of the flap valve (and thus no respiration) occurs within a pre-set time. Alternatively, the audible alarm can be configured to sound if a respiration event does occur.

In a preferred embodiment, the device is configured to sense the number of actuations of flap valve per unit of time and report a respiration rate of a patient on numerical display 20. Numerical display is preferably an LED or like visually sensed medium or display. As will be appreciated by one of ordinary skill in the art, visual displays and audible alarms are preferred for many reasons. For example, such alarms not only allow for quick determination of a patient's status, they also allow the patient's status to be monitored in high-noise environments, such as during the transport of injured via helicopter or fixed wing aircraft. These advantages are particularly acute in situations such as those posed by chemical warfare, wherein non-contact monitoring means for use by medics are needed.

In a preferred embodiment, depicted in FIG. 5A, outer face 41 of outer portion 40 of outlet 13 is removable from monitor 1. Allowing the outer portion 40 of body 10 to be moved, allows a user to place the reporting features, i.e., lamps, LED, respiration rate, in a position of optimum visibility. In accordance with this embodiment, outer face 41 includes display and/or on/off switch 18 and is in electrical communication with battery circuit 16 via wires (not shown). Wires are preferably made retractable such that outer face can be selectively removed and re-attached to body 10. Alternatively, wireless communication means may be used instead of wires.

In another preferred embodiment, depicted in FIG. 5B, just a removable display feature 50, which may or may not include both the light and/or LED display of respiration rate, is removable from outer face 41. A coil of wire 51 attached to the display feature or other suitable means may be used to allow removal and retraction of the display. Alternatively, wireless communication means may be used to communicate respiration information from the device to the removable display.

In yet another preferred embodiment, depicted in FIG. 6, monitor 1 makes use of wire 51 attached to display 50 having separate indicators 63, 64 for the presence or absence of respiration. Alternatively, wireless communication means may be used. In the embodiment of FIG. 6, flap valve 14 uses sensing means 16 which provides information to a user depending on the position of the flap. As depicted, the device has a first contact 61 and a second contact 62. The first contact 61 is engaged by flap 15 when flap valve 14 of monitor 1 is in a closed position (depicted in FIG. 6). Engagement with first contact 61 results in the completion of an electrical circuit which results in a signal being sent down wire 51 and illuminating a red indicator lamp 63 or a "no respiration" light. However, if flap 15 moves in response to a respiration event, flap 15 engages second contact 62, thereby completing a different electrical circuit which results in a signal being sent down wire 51 and illuminating a green indicator lamp 64 or "breathing detected" light. Any suitable electrical wiring or logic circuitry may be used to effectuate this aspect of the invention. Likewise, these aspects of this embodiment of the flap valve sensing means may be used with other previously described embodiments of the invention and other sensing means for detecting respiration.

As best depicted in FIG. 3, to facilitate use of monitoring device 1, a seal 21 is provided on the air outlet 13 end of air passageway 11. The seal 21 is preferably configured to permit fluid-tight engagement with the flange 33 of an air input orifice 32 of an air filter canister 31 of a gas mask 30, such as an M40 or other gas mask. The seal 21 may be comprised of any suitable material capable of providing fluid-tight connection to the flange 33 of the orifice 32. Presently preferred materials include rubber and other resiliently deformable materials. The term "seal" is meant to include any grommet, washer or seal which is adapted to facilitate fluid-tight connection.

The monitoring device 1 and orifice 32 may be couple by any suitable means. Preferably, the monitor 1 and orifice 32 may be mechanically coupled. More preferably, the monitor 1 and orifice 32 are removably mechanically coupled. For example, the monitor 1 and mask 30 may be configured to allow the device to be snapped into a fitting associated with the orifice or screwed onto mating threads associated with the orifice. Alternatively, the monitor 1 and mask 30 may be in an integral unit. For example, the monitor 1 may be integrally attached to the mask 30 and only removable, if at all, for repair or replacement. In a preferred embodiment, the monitor's seal 21 couples with flange 33.

In an alternative embodiment not depicted, the monitor 1 is configured to encircle a portion of the body of canister 31 or the entire canister. In accordance with this embodiment, the monitor 1 may include an elastomeric or other stretchably deformable material which allows the body to mate fluid-tight with the body of the canister 31. In accordance with this embodiment, the device is preferably adapted to accommodate fluid-tight sealing with a variety of differently sized and shaped canisters and/or orifices.

In yet another alternative embodiment, the monitor 1 is configured to encircle the mouth and/or nares of a patient. As will be appreciated, such a device can be used with patient's wearing paper masks or no masks at all. According to this embodiment, the device can be secured to the patient by any suitable means, for example, using an elastic band which may be placed around the patient's head to hold the mask in place over the mouth and/or nares.

The embodiments of the invention described above provide for use of the monitoring device of the invention with or without a gas mask, provide for coupling the monitor to a gas mask canister orifice, and provide for coupling the monitor with a mask by surrounding a portion of the canister. The embodiments also provide for the monitoring device to be integrated into existing masks, and thus always present on the masks, and provide for the monitoring device to be separate and thus only used selectively by medical personnel and the like when the mask wearer is unconscious.

As will be appreciated, the compact and lightweight design of the present invention, coupled with the relative inexpense provides numerous benefits as well. Likewise, the durable construction and reliability of the device and its features makes it suited for battlefield environments, high vibration environments, and high noise environments.

A particularly advantageous aspect of the invention is realized by the features of the aforementioned embodiments of the invention. Specifically, there is no known device available for determining whether casualties in Level IV MOPP gear or healthy personnel wearing gas masks are breathing. The present invention provides a small and lightweight device, thereby allowing a medic to carry several. Thus, a battlefield medic is enabled to rapidly attach the devices to the gas mask filter canisters of casualties to detect and/or monitor respiration by visual and audible means. In addition, the device can be configured to send a signal to a remote location indicting the wearer is (or is not) breathing, or, for example, the type and/or frequency of respiration events. Accordingly, this device will facilitate triage in mass casualty situations by using respiration as a proxy for finding a pulse on a patient.

Accordingly, as will be appreciated, the present invention provides the combat medic with the first non-contact triage device for use in chemical and biological mass casualty situations, and also provides a reliable respiration monitor for firefighters or other personnel wearing gas masks.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

I claim:

1. A respiration monitoring device comprising:
   a body having an inlet and an outlet in fluid communication;
   a connector having a sealing surface on said air outlet end of said body, wherein said sealing surface is adapted to permit fluid-tight engagement with an air input orifice of an air filter canister of a gas mask;
   a detector disposed between said inlet and said outlet comprising a flap-valve switch actuatable by respiration air of a wearer of said gas mask;
   a logic circuit configured to report respiration actuated movement of said flap-valve; and
   a battery for powering said logic circuit.

2. The monitoring device of claim 1 further comprising a visual display electrically coupled to said logic circuit.

3. The monitoring device of claim 2 wherein said visual display comprises a light that is illuminated upon completion of a circuit caused by movement of said flap-valve into an open position.

4. The monitoring device of claim 1 further comprising an audible alarm electrically coupled to said logic circuit.

5. The monitoring device of claim 4 wherein said audible alarm is sounded upon completion of a circuit caused by movement of said flap-valve into an open position.

6. The monitoring device of claim 1 further comprising a visual display which displays a value corresponding to a number of air actuated movements of said flap-valve from an open position to a closed position in a given period of time.

7. The monitoring device of claim 1 wherein said flap valve switch is actuatable from a first position wherein it is in engagement with a first contact and a second position wherein it engages a second contact.

8. The monitoring device of claim 7 wherein engagement with said first contact illuminates a red lamp and engagement with said second contact results in illumination of a green lamp.

9. The monitoring device of claim 1 wherein said monitoring device is sealed to a flange of said air input orifice of said air filter canister.

10. The monitoring device of claim 1 wherein said monitoring device is sealed around a portion of an air filter canister body.

11. The monitoring device of claim 1 further comprising an on/off switch associated with said battery.

12. The monitoring device of claim 1 further comprising a selectively removable visual display mounted on an inlet side face of said body.

13. The monitoring device of claim 1 wherein said body includes a removable outer portion on an inlet end; said outer portion having a visual display disposed thereon.

14. A non-contact respiration monitor comprising:
   a monitor body having an inlet, an outlet and a fluid monitoring chamber passing therethrough; said monitor body having a connector having a sealing surface on said outlet end configured to permit fluid-tight engagement with an air input orifice of an air filter canister of a gas mask an air flow actuated flap-valve switch, said switch being actuated by the respiration of a wearer of said gas mask;

a battery powered logic circuit operatively associated with said flap-valve switch; and a means for reporting the presence or absence of respiration.

15. The respiration monitor of claim 14 further comprising an on/off switch operatively associated with said battery.

16. The respiration monitor of claim 15 wherein said means for reporting the presence or absence of respiration comprises a visually detectable light which is electrically illuminated when respiration moves said flap-valve to an open position.

17. The respiration monitor of claim 16 wherein said means for reporting the presence or absence of respiration includes an audible detectable alarm which is electrically sounded when respiration moves said flap-valve to an open position.

18. The respiration monitor of claim 17 wherein said means for reporting the presence or absence of respiration further includes a visual display of a rate of respiration calculated by said logic circuit based.

19. A method of using a respiration monitor comprising:

disposing a monitor body having an inlet, an outlet and a fluid monitoring chamber passing therethrough in fluid tight contact with the outside end of a gas mask; whereby respiration of a wearer of said gas mask draws air through said monitor, then into said gas mask, and then to the lungs of the user;

activating a battery powered logic circuit configured to sense air movement in said fluid monitoring chamber;

detecting the presence or absence of air passing from said inlet to said outlet, and determining the presence or absence of respiration.

20. The method of claim 19 wherein said monitor is disposed around an air inlet of said gas mask.

21. The method of claim 19 wherein said monitor is coupled to an air inlet of said gas mask.

22. The method of claim 19 wherein said monitor is disposed around an air inlet of said gas mask filter canister.

23. The method of claim 19 wherein said monitor is coupled to an air inlet of said gas mask filter canister.

* * * * *